United States Patent
Boures et al.

(10) Patent No.: US 6,475,991 B2
(45) Date of Patent: *Nov. 5, 2002

(54) USE OF α-ALKYLGLUCOSIDES AND α-ALKYLGLUCOSIDE ESTERS AS ANTI-MICROBIAL AN AGENTS

(75) Inventors: Emmanuel Boures, Clermont-Ferrand (FR); Arnaud Messager, Riom (FR)

(73) Assignee: Ulice (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 40 days.

(21) Appl. No.: 09/197,798

(22) Filed: Nov. 23, 1998

(65) Prior Publication Data

US 2001/0029247 A1 Oct. 11, 2001

Related U.S. Application Data

(63) Continuation of application No. PCT/FR97/00913, filed on May 23, 1997.

(30) Foreign Application Priority Data

May 24, 1996 (FR) .............................. 96 06517

(51) Int. Cl.$^7$ ..................... A61K 31/70; C12P 19/44; C08B 31/02

(52) U.S. Cl. .............................. 514/25; 435/74; 435/97; 435/99; 435/105; 435/134; 435/135; 536/4.1; 536/102; 536/107; 536/124

(58) Field of Search .............................. 435/74, 97, 99, 435/105, 134, 135; 536/4.1, 102, 107, 124; 514/25

(56) References Cited

U.S. PATENT DOCUMENTS 5,773,256 A * 6/1998 Pelenc et al. .................. 435/74

FOREIGN PATENT DOCUMENTS

FR   PCT/FR92/00782   8/1992

OTHER PUBLICATIONS

J. Am. Oil Chem. Soc., vol. 67, No. 12, pp. 996–1001, Dec. 1990.*

* cited by examiner

Primary Examiner—Gary Geist
Assistant Examiner—Howard V. Owens, Jr.
(74) Attorney, Agent, or Firm—Lerner, David, Littenberg, Krumholz & Mentlik, LLP

(57) ABSTRACT

The present invention embraces methods and compositions which employ antimicrobial compositions which are α-alkylglucosides and esters thereof.

21 Claims, 7 Drawing Sheets

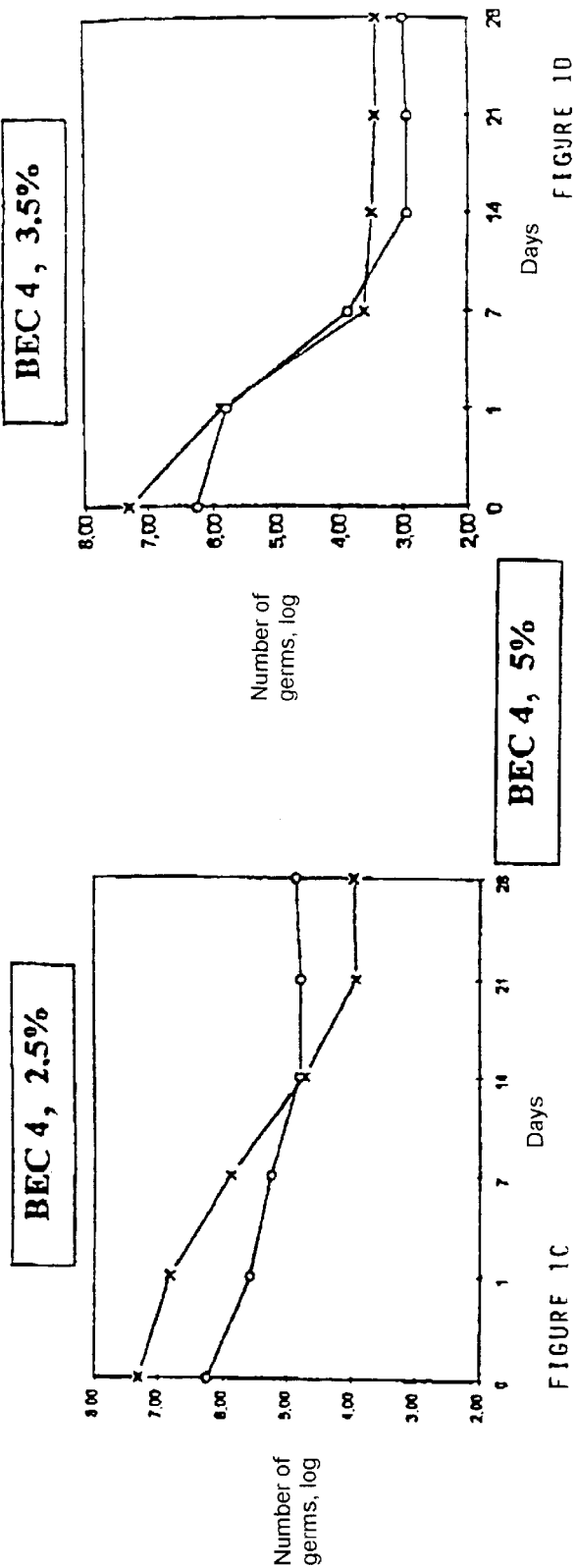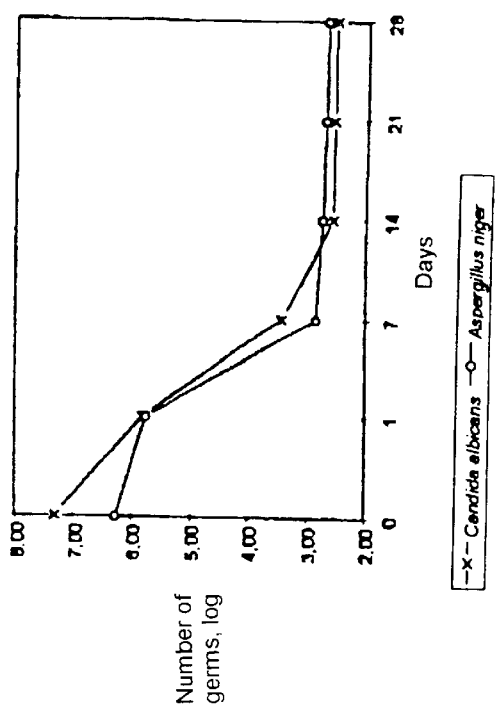

USE OF α-ALKYLGLUCOSIDES AND α-ALKYLGLUCOSIDE ESTERS AS ANTI-MICROBIAL AN AGENTS

This is a Continuation of PCT/FR97/00913, filed May 23, 1997.

FIELD OF THE INVENTION

The present invention relates to the use of α-alkylglucosides and/or α-alkylglucoside esters, more particularly to α-butylglucoside esters, as an antimicrobial agent, in particular an antibacterial and/or antifungal agent, in the preparation of pharmaceutical, cosmetic or agro-alimentary compositions, or other types of compositions when such an antimicrobial agent needs to be present. The invention also relates to specific compositions for such uses which comprise such antimicrobial agents.

BACKGROUND OF THE INVENTION

Protecting cosmetic, dermatological, pharmaceutical and agro-alimentary products against possible microbial development necessitates the use of preservatives. However, the majority of preservatives in current use, in particular in cosmetics and in topical patent medicines, tend to cause skin and eye irritation. Further, they may be incompatible with the components used, in particular some surfactants.

Sugar or alkylglucoside fatty acid esters are known for their emulsifying and conditioning properties for the hair and for skin. Their use in cosmetics has been described in a number of articles and patent applications.

SUMMARY OF THE INVENTION

The inventors have unexpectedly discovered that α-alkylglucoside esters have bactericidal and/or fungicidal properties in addition to their known emulsifying properties. In parallel, it has been discovered that α-alkylglucosides, some of which could constitute the substrate for the esterification reaction providing said esters, also have certain antimicrobial properties, in particular bactericidal properties.

One aim of the present invention is thus to provide means for effectively preventing or reducing microbial development in a medium which is suitable therefor, while avoiding the problems inherent in using some types of preservatives as mentioned above.

In a first aspect, then, the invention concerns the use in a composition, in particular in a pharmaceutical, cosmetic or agro-alimentary composition, of an α-alkylglucoside component or an α-alkylglucoside ester component or a mixture thereof, as a microbicidal agent, in particular a bactericide or fungicide or both at the same time, said component or said mixture being in a proportion which is sufficient to preserve said composition from microbial development, in particular bacterial or fungal development, or both at the same time.

Clearly, the present invention also encompasses the use of mixtures of at least two different α-alkylglucoside ester and/or α-alkylglucoside components.

DESCRIPTION OF THE PREFERRED EMBODIMENTS

The preserving property of such compounds thus provides a "self-protecting" effect against microbial contamination of pharmaceutical, cosmetic, dermatological or agro-alimentary formulations. α-alkylglucoside esters, in particular α-butylglucoside esters, can be obtained by enzymatic esterification using an α-alkylglucoside such as that described in International patent PCT/FR92/00782. The products obtained by that process are stereospecific (α) and are normally monoglucosides. Because of the absence of β anomer in the products used in the present invention, certain physical characteristics, such as the melting point and the solubility of the alkylglucoside, are defined very precisely.

α-alkylglucosides are preferably esterified in the $C_6$ then the $C_2$ position. This enzymatic esterification is catalysed by enzymatic preparation with a lipase activity. The reaction conditions can either enrich the proportion of α-alkylglucoside monoester, mainly with esterification at $C_6$, or enrich the proportion of diester, with esterification mainly at $C_2$ and $C_6$. The process can esterify both saturated fatty acids and unsaturated fatty acids.

Such esters are stereospecific, chemically pure and completely characterized. They are also not mixed with secondary products, provided that they are obtained by an entirely enzymatic synthesis process. Since these α-alkylglucoside esters are also non toxic and non irritating emulsifying agents, they are particularly suitable for cosmetic, pharmaceutical or alimentary use.

The α-alkylglucoside ester component, α-alkylglucoside component or mixture thereof is preferably in a proportion in the range from about 0.5% to 10%, preferably in the range about 2.5% to 5% by weight of said composition.

Further, when acting as a bactericidal agent, the α-alkylglucoside ester component is in a proportion of at least about 3.5%, preferably 5%, by weight of the composition.

The alkyl group of the α-alkylglucoside or the α-alkylglucoside ester is preferably a group containing 1 to 6 carbon atoms, preferably a butyl group.

The α-butylglucoside ester preferably represents at least 40%, preferably 80%, by weight of bactericidal and/or fungicidal agent.

Particularly preferably, the α-alkylglucoside ester is an α-butylglucoside mono- or di-caprate, an α-butylglucoside mono- or di-palmitate, or an α-butylglucoside mono- or di-cocoate.

Laurates, myristates and stearates are esters which can also be used.

As described above, the inventors have also discovered the bactericidal and fungicidal properties of α-alkylglucosides. In a preferred use of the present invention, when used as a bactericidal agent, the α-alkylglucoside component is in a proportion in the range about 0.8% to 5% by weight of the composition, and when used as a fungicidal agent, it is in a proportion in the range about 1% to 3% by weight of the composition.

The microbicidal activity of the above components may vary to a certain extent depending on the conditions of use. The skilled person is clearly at liberty to adapt these conditions to obtain the desired microbicidal effect.

The present invention also relates to a pharmaceutical, cosmetic or agro-alimentary composition the active principle of which comprises an α-alkylglucoside ester, an α-alkylglucoside or a mixture thereof, the alkyl group of which contains 1 to 6 carbon atoms. Preferably, this active principle is present in an amount of 0.5% to 10%, preferably 2.5% to 5%, by weight with respect to said composition.

Preferably, the alkyl group of the α-alkylglucoside and/or α-alkylglucoside ester is a group containing 1 to 6 carbon atoms, preferably a butyl group.

In a preferred composition of the invention, the α-alkylglucoside ester is an α-butylglucoside mono- or di-caprate, an α-butylglucoside mono- or di-palmitate, or an α-butylglucoside mono- or di-cocoate.

In a particularly preferred composition, the active principle is constituted by one of the following mixtures a), b), c) or d):

| | | |
|---|---|---|
| a) | Polyethylene glycol (30) dipolyhydroxystearate | 15% |
| | α-butylglucoside monocaprate | 48% |
| | α-butylglucoside dipalmitate | 37% |
| b) | Ester of polyethylene oxide and a fatty alcohol | 40% |
| | Ether of polyethylene glycol (21) and stearic alcohol | 15% |
| | α-butylglucoside monocaprate | 26% |
| | α-butylglucoside monopalmitate | 19% |
| c) | Ester of citric acid and glyceryl sorbitol | 20% |
| | α-butylglucoside monocaprate | 46% |
| | α-butylglucoside monopalmitate | 34% |
| d) | α-butylglucoside dicocoate | 48% |
| | α-butylglucoside monococoate | 37% |
| | α-butylglucoside monopalmitate | 15% |

These mixtures a), b), c) and d) are respectively termed: BEC 4, BEC 721985, BEC SCS and BEC SH.

Preferably again, the pH of the composition of the invention is in the range 3 to 10, and preferably about 5.

The present invention also relates to a process for preparing an α-alkylglucoside ester for use in accordance with the invention, in which said α-alkylglucoside ester is obtained by stereospecific enzymatic esterification of α-butylglucoside in the presence of a thinning agent, in particular hexane.

The present invention also relates to a process for external antimicrobial treatment, in particular in man, in which the α-alkylglucoside and α-alkylglucoside ester type compounds described above act as anti-bactericidal and/or anti-fungal agents, in different galenical forms.

The inventors thus tested the bactericidal and/or fungicidal activity of α-alkylglucoside and α-alkylglucoside ester type compounds to determine the conditions, in particular the concentrations, under which said compounds have to be used for the desired activities to be obtained. The results of these tests were analysed in accordance with the "Pharmacopée Française" which describes a methodology for monitoring the efficacy of antimicrobial preservation agents in pharmaceutical preparations and establishes minimum efficacy criteria as a function of the administration routes of a medicine. Thus specific criteria are fixed for topical patent medicines which can be considered to be close to cosmetic products in their conception. The recommended and significant criteria for bactericidal and/or fungicidal activity of a product are:

for a bactericidal effect (*Staphylococcus aureus, Pseudomonas aeruginosa, Escherichia coli*):
  reduction of 3 logarithmic units in 14 days with respect to the initial population;
  no increase in microbial growth after 14 days and up to the 28$^{th}$ day, when the test is stopped;
for a fungicidal effect (yeasts and moulds) (*Candida albicans, Aspergillus niger*):
  reduction of one logarithmic unit in 14 days with respect to the initial population;
  no increase in microbial growth after 14 days and up to the 28$^{th}$ day, when the test is stopped.

Expression of Results

In order to facilitate visualisation of the bactericidal or fungicidal effect of the tested compounds, the results obtained were transcribed into the graphical forms of FIG. 5 which show the reduction in the number of germs in logarithmic units, over time (1 day, 7 days, 14 days, 21 days, 28 days).

Figure 1A:
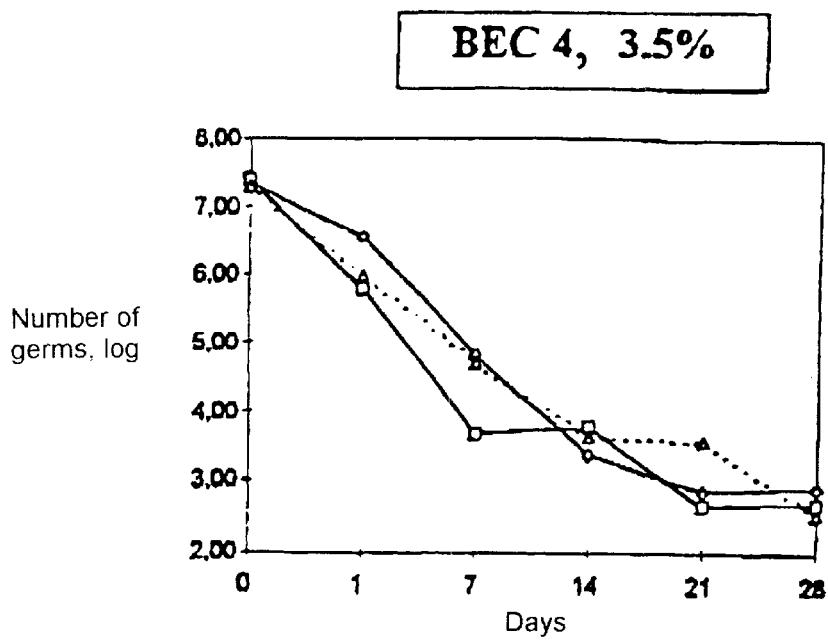
FIG. 1 shows the antimicrobial activity of mixture BEC 4, showing the reduction in the number of bacterial germs (log) (FIGS. 1A and 1B) and fungal germs (FIGS. 1C, 1D, 1E) at different concentrations, as a function of time (days) in different strains.
Figure 1B:
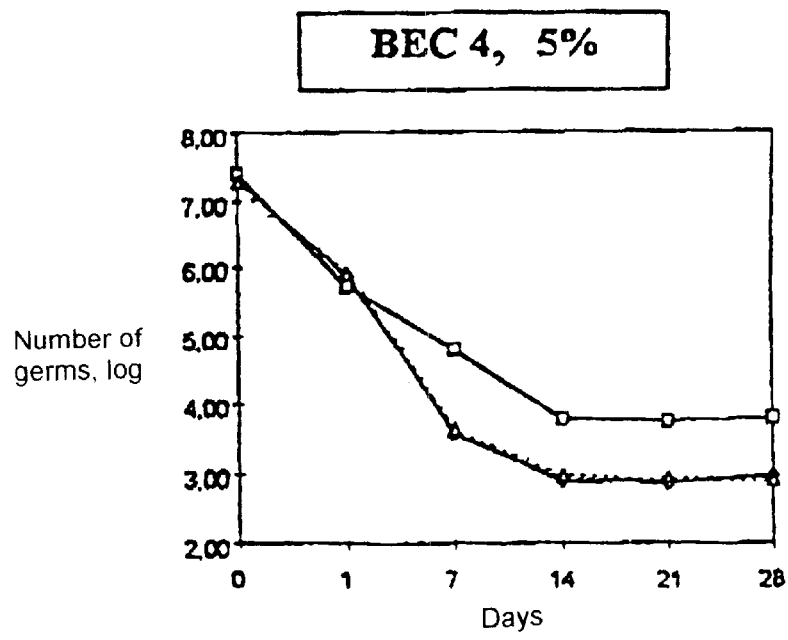
Figure 2A:
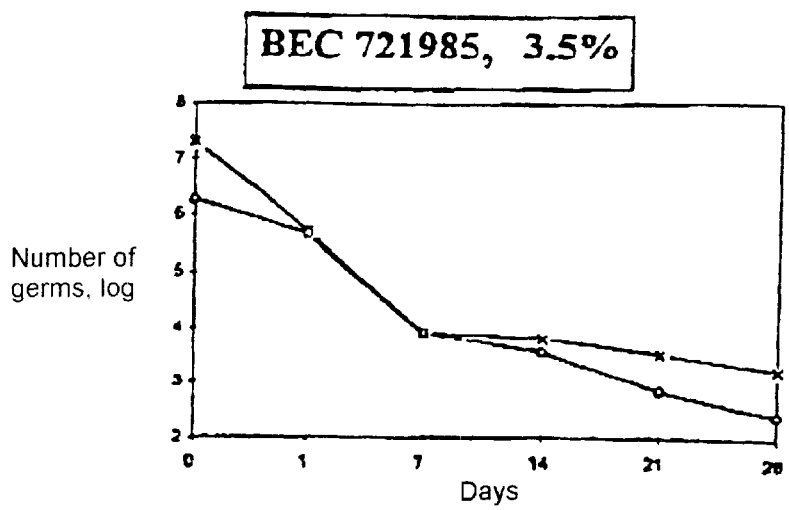
FIG. 2 shows the antimicrobial activity of mixture BEC 721985, showing the reduction in the number of bacterial germs (log) (FIG. 2C) and fungal germs (FIGS. 2A and 2B) at different concentrations, as a function of time (days) in different strains.
Figure 2B:
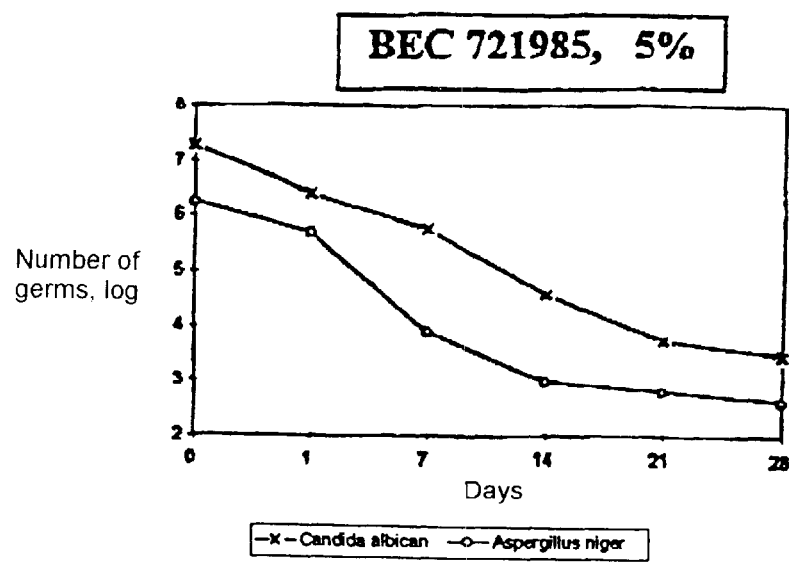
Figure 2C:
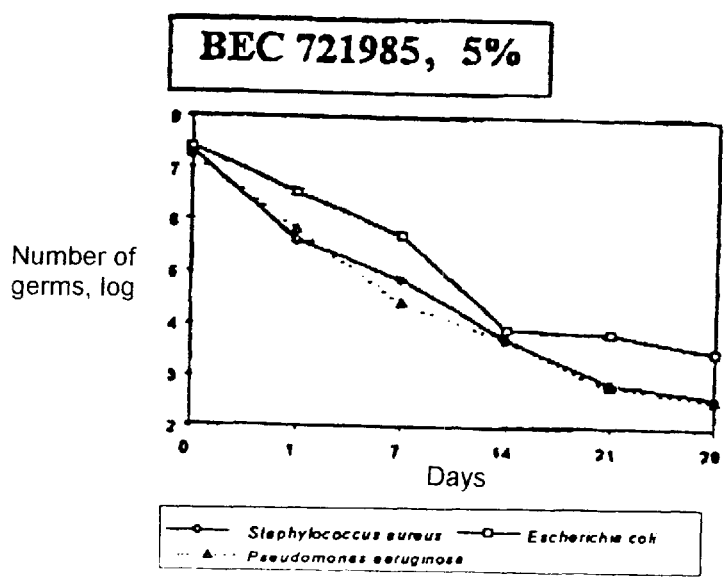
Figure 3A:
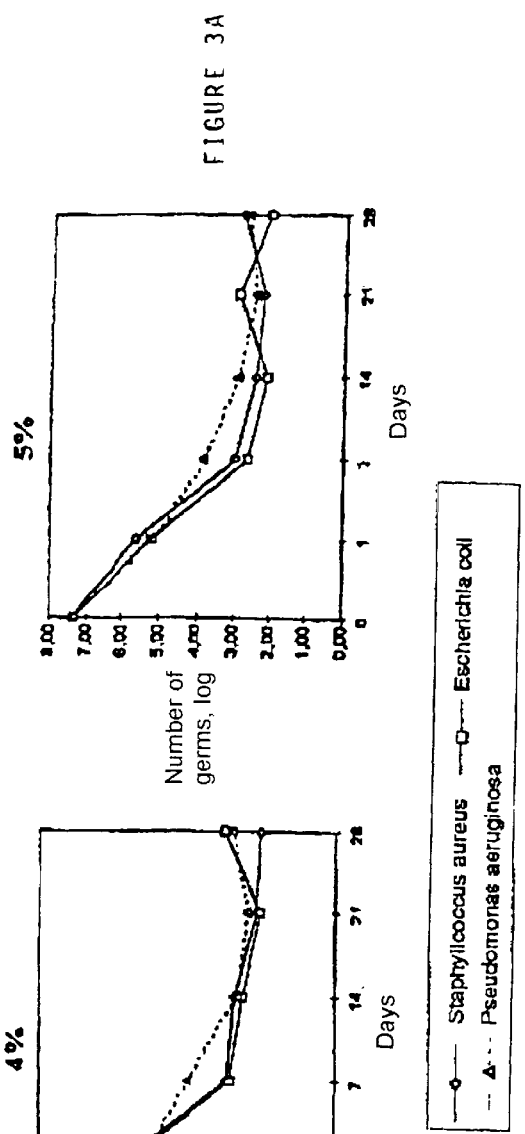
FIG. 3 shows the antimicrobial activity of mixture BEC SCS, showing the reduction in the number of bacterial germs (log) (FIG. 3A) and fungal germs (FIG. 3B) at different concentrations, as a function of time (days) in different strains.
Figure 3B:
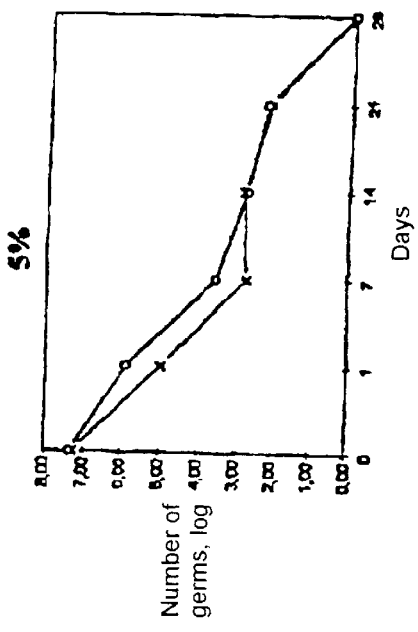
Figure 4A:
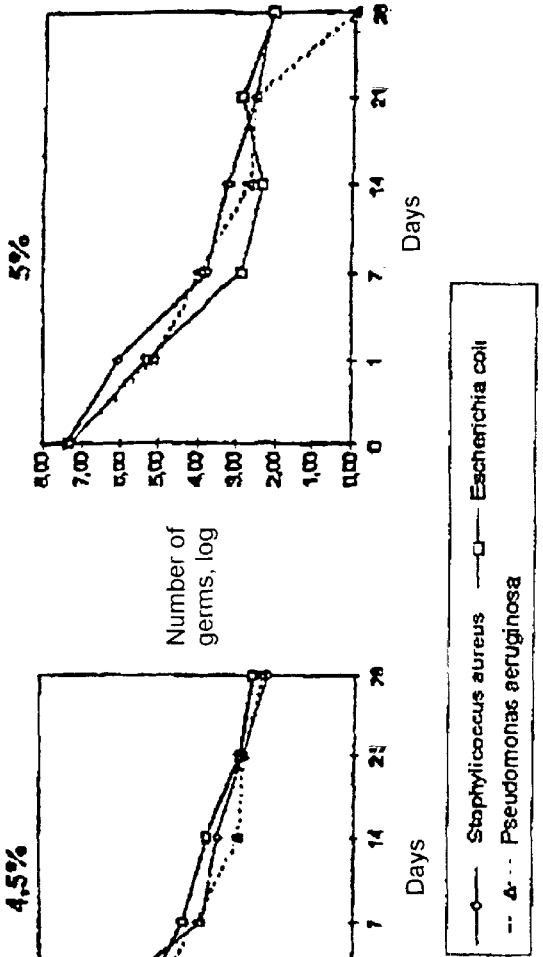
FIG. 4 shows the antimicrobial activity of mixture BEC SH, showing the reduction in the number of bacterial germs (log) (FIG. 4A) and fungal germs (FIG. 4B) at different concentrations, as a function of time (days) in different strains.
Figure 4A:
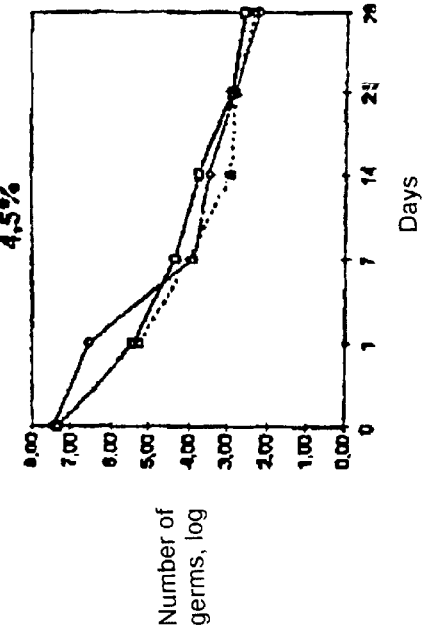
Figure 4B:
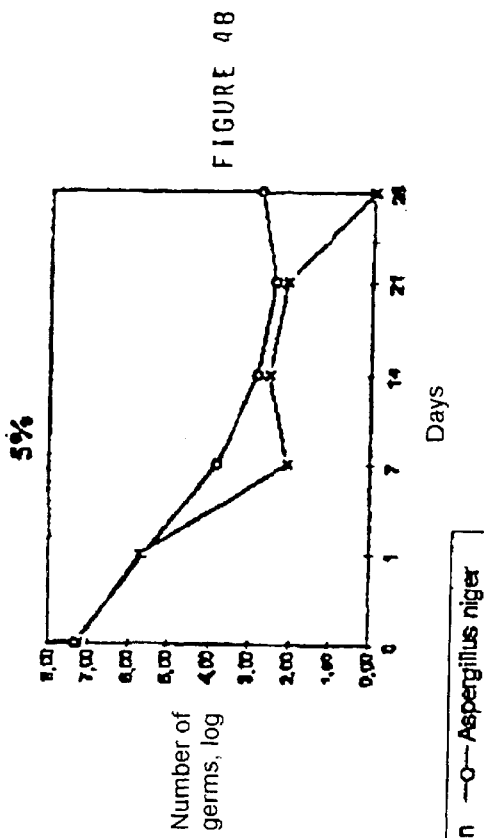
Figure 4B:
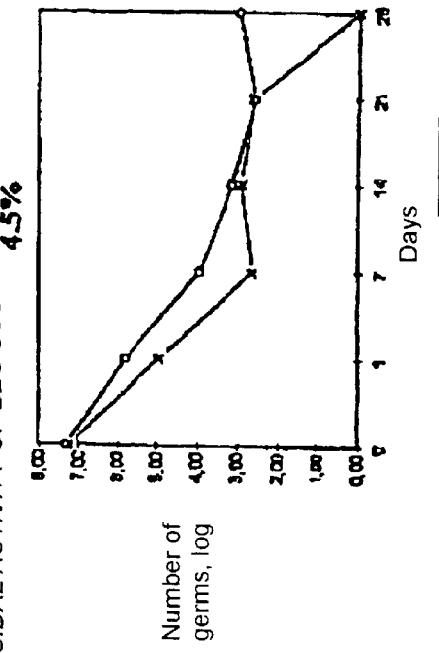
Figure 5A:
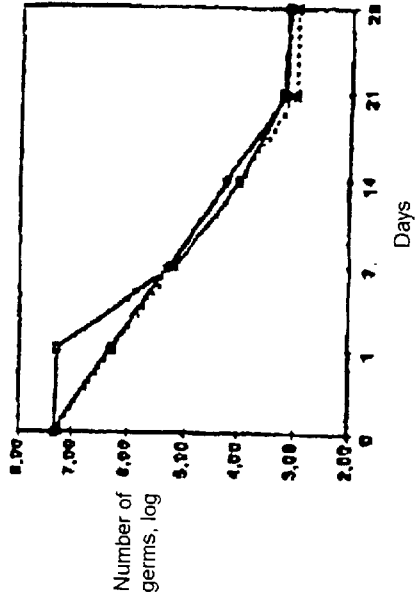
FIG. 5 shows the antimicrobial activity of α-alkylglucosides, showing the reduction in the number of bacterial germs (log) (FIG. 5A) and fungal germs (FIG. 5B) at different concentrations, as a function of time (days) in different strains.
Figure 5A:
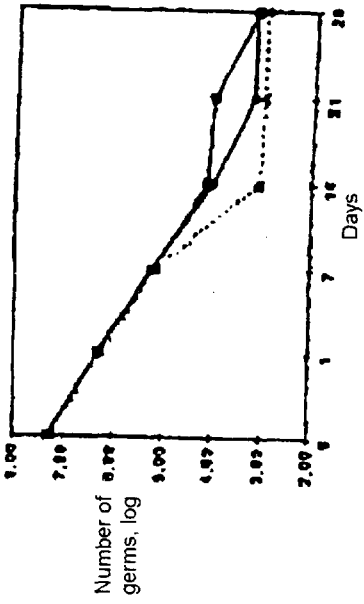
Figure 5A:
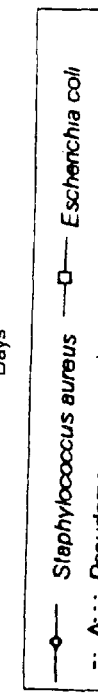
Figure 5A:
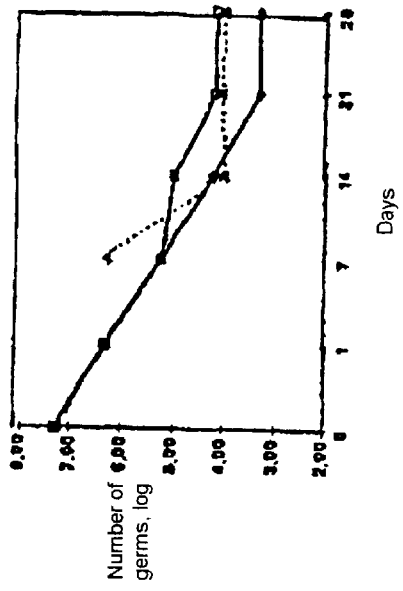
Figure 5A:
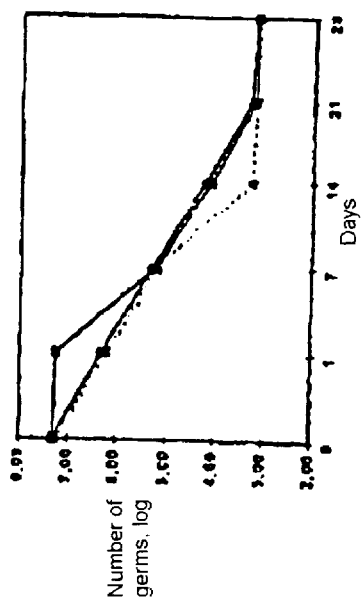
Figure 5A:
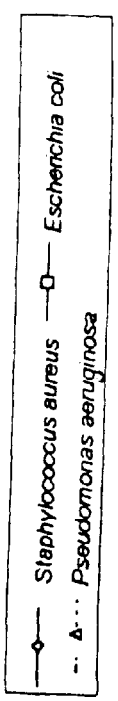
Figure 5B:
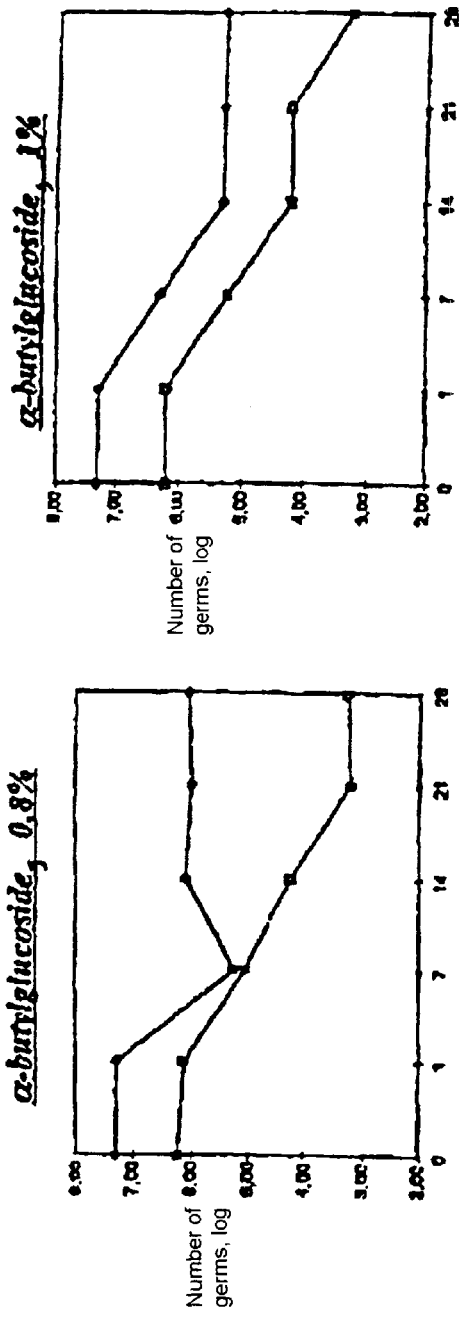
Figure 5B:
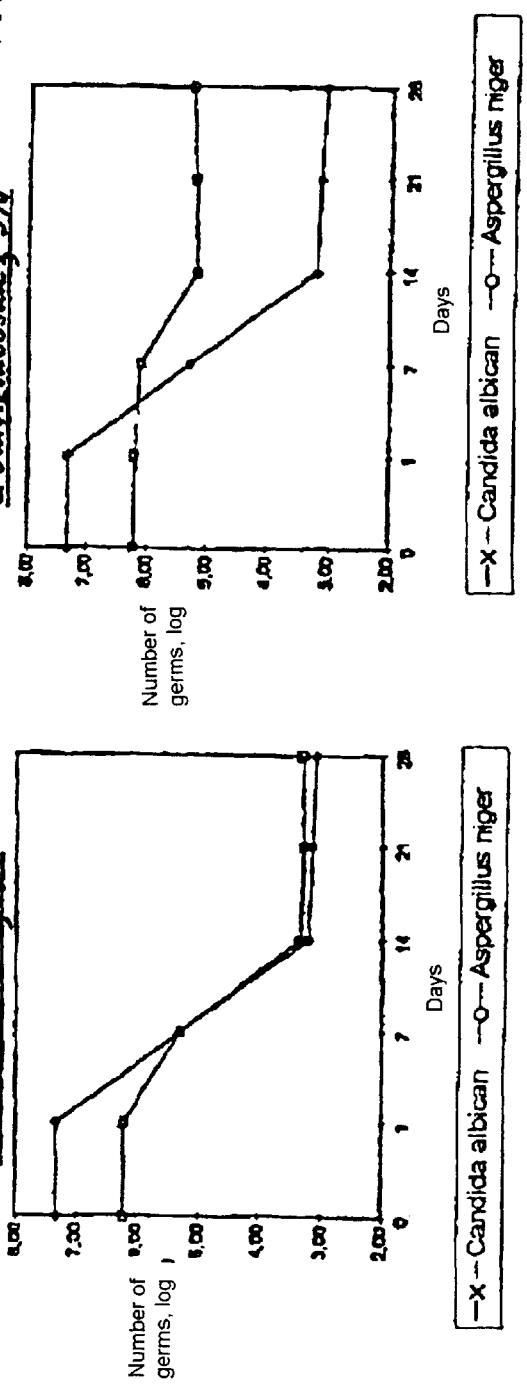

The results are also shown in the form of tables (see below) showing the logarithmic reductions obtained for the different bacterial or fungal strains on which the tests were carried out.

ANTIMICROBIAL ACTIVITY

The tests carried out demonstrated the antimicrobial activity of certain types of compounds or certain mixtures of compounds. Clearly, the following compounds or mixtures which constitute the active agents, do not in any way limit the scope of the present invention.

A/Antimicrobial Activity of α-alkylglucoside Monocaprates
Bactericidal and Fungicidal Properties of 3% 3.5%, 4%, 4.5% and 5% α-butylglucoside (α-BG) Monocaprate

| 3% α-butylglucoside monocaprate | | Logarithmic reduction | | | | |
|---|---|---|---|---|---|---|
| | | 1 d | 7 d | | 21 d | 28 d |
| Bacteria | *Staphylococcus aureus* | 1.7 | 2.3 | | 3.8 | 4.4 |
| | *Escherichia coli* | 1.4 | 3.6 | | 4.3 | ST |
| | *Pseudomonas aeruginosa* | 1.5 | 2.6 | | 3.8 | 4.6 |
| Yeast | *Candida albicans* | 1.6 | 2.3 | | 4.3 | 4.5 |
| Fungus | *Aspergillus niger* | 0.5 | 1.7 | | 4.3 | 4.2 |

ST: complete sterility, disappearance of stains

-continued

| 3.5% α-butylglucoside monocaprate | | Logarithmic reduction | | | | |
|---|---|---|---|---|---|---|
| | | 1 d | 7 d | 14 d | 21 d | 28 d |
| Bacteria | Staphylococcus aureus | 2.4 | 3.3 | | 4.3 | 5.1 |
| | Escherichia coli | 2.2 | 3.4 | | 4.5 | ST |
| | Pseudomonas aeruginosa | 2.7 | 3.5 | | 4.5 | 5.0 |
| Yeast | Candida albicans | 2.6 | 3.4 | | 4.6 | ST |
| Fungus | Aspergillus niger | 2.3 | 3.4 | | 4.3 | 4.6 |

ST: complete sterility, disappearance of stains

| 4% α-butylglucoside monocaprate | | Logarithmic reduction | | | | |
|---|---|---|---|---|---|---|
| | | 1 d | 7 d | 14 d | 21 d | 28 d |
| Bacteria | Staphylococcus aureus | 3.3 | 3.7 | | 4.8 | ST |
| | Escherichia coli | 2.3 | 3.4 | | 5.0 | ST |
| | Pseudomonas aeruginosa | 2.9 | 4.9 | | ST | ST |
| Yeast | Candida albicans | 2.2 | 3.4 | | 4.7 | ST |
| Fungus | Aspergillus niger | 2.5 | 3.4 | | 4.4 | 4.9 |

ST: complete sterility, disappearance of stains

| 4.5% α-butylglucoside monocaprate | | Logarithmic reduction | | | | |
|---|---|---|---|---|---|---|
| | | 1 d | 7 d | 14 d | 21 d | 28 d |
| Bacteria | Staphylococcus aureus | 3.5 | 3.9 | | ST | ST |
| | Escherichia coli | 2.4 | 3.6 | | 4.8 | ST |
| | Pseudomonas aeruginosa | 3.7 | 4.1 | | ST | ST |
| Yeast | Candida albicans | 2.4 | 3.5 | | ST | ST |
| Fungus | Aspergillus niger | 2.5 | 3.5 | | 4.5 | ST |

ST: complete sterility, disappearance of stains

| 5% α-butylglucoside monocaprate | | Logarithmic reduction | | | | |
|---|---|---|---|---|---|---|
| | | 1 d | 7 d | 14 d | 21 d | 28 d |
| Bacteria | Staphylococcus aureus | 3.5 | 4.8 | | ST | ST |
| | Escherichia coli | 2.3 | 3.9 | | 4.8 | ST |
| | Pseudomonas aeruginosa | 3.8 | 4.6 | | ST | ST |
| Yeast | Candida albicans | 2.4 | 3.7 | | 5.0 | ST |
| Fungus | Aspergillus niger | 2.7 | 3.4 | | ST | ST |

ST: complete sterility, disappearance of stains

B/Antimicrobial Activity of α-alkylglucoside Esters

α-alkylglucoside esters, more particular of α-butylglucoside, were combined or not combined with other components to form the following "BEC" compounds:

| BEC 4 | Polyethylene glycol (30) dipolyhydroxystearate | 15% |
| | α-butylglucoside monocaprate | 48% |
| | α-butylglucoside dipalmitate | 37% |
| BEC 721 985 | Ester of polyethylene oxide and a fatty alcohol | 40% |
| | Ether of polyethylene glycol (21) and stearic acid | 15% |
| | α-butylglucoside monocaprate | 26% |
| | α-butylglucoside monopalmitate | 19% |
| BEC SCS | Ester of citric acid and glyceryl sorbitol, mixture | 20% |
| | α-butylglucoside monocaprate | 46% |
| | α-butylglucoside monopalmitate | 34% |
| BEC SH | α-butylglucoside dicocoate | 48% |
| | α-butylglucoside monococoate | 37% |
| | α-butylglucoside monopalmitate | 15% |

The proportion of the above mixtures in the different compositions was expressed in the following tables as a percentage by weight with respect to said composition.

I—Antimicrobial Efficacy of Mixture BEC 4 a) Bactericidal Activity of BEC 4 Mixture, 3.5% and 5% by Weight with Respect to the Total Composition

| STRAINS | 1 DAY | 7 DAYS | 14 DAYS | 21 DAYS | 28 DAYS |
|---|---|---|---|---|---|
| Staphylococcus aureus | 0.8 | 2.5 | | 4.5 | 4.4 |
| Escherichia coli | 1.6 | 3.7 | | 4.7 | 4.7 |
| Pseudomonas aeruginosa | 1.3 | 2.6 | | 3.7 | 4.7 |

3.5% BEC 4

| STRAINS | 1 DAY | 7 DAYS | 14 DAYS | 21 DAYS | 28 DAYS |
|---|---|---|---|---|---|
| Staphylococcus aureus | 1.4 | 3.7 | | 4.5 | 4.4 |
| Escherichia coli | 1.7 | 2.6 | | 3.6 | 3.6 |
| Pseudomonas aeruginosa | 1.4 | 3.6 | | 4.4 | 4.4 |

5% BEC 4

In accordance with the specifications of the "Pharmacopée Française", the BEC 4 mixture induced a large bactericidal effect at 3.5% with a logarithmic reduction of more than 3 after 14 days. This effect was increased for a concentration of 5%, in particular for the Staphylococcus aureus and Pseudomonas aeruginosa strains.

b) Fungicidal Activity of BEC 4 Mixture, 2.5%, 3.5% and 5% by Weight with Respect to the Total Composition

| STRAINS | 1 DAY | 7 DAYS | 14 DAYS | 21 DAYS | 28 DAYS |
|---|---|---|---|---|---|
| Candida albicans | 0.5 | 1.4 | | 3.4 | 3.3 |
| Aspergillus niger | 0.7 | 1.0 | | 1.5 | 1.4 |

2.5% BEC 4

| STRAINS | 1 DAY | 7 DAYS | 14 DAYS | 21 DAYS | 28 DAYS |
|---|---|---|---|---|---|
| Candida albicans | 1.4 | 3.7 | | 3.9 | 3.9 |
| Aspergillus niger | 0.5 | 2.4 | | 3.3 | 3.3 |

3.5% BEC 4

| STRAINS | 1 DAY | 7 DAYS | 14 DAYS | 21 DAYS | 28 DAYS |
|---|---|---|---|---|---|
| Candida albicans | 1.5 | 3.9 | | 4.7 | 4.8 |
| Aspergillus niger | 0.5 | 3.4 | | 3.5 | 3.6 |

5% BEC 4

In accordance with the specifications of the "Pharmacopée Française", the BEC 4 mixture induced a fungicidal effect which was higher than the minimum requirements. This effect increased substantially with the increasing concentrations used. Thus for Candida albicans, the logarithmic reductions were 2.6/3.8/4.7 for concentrations of 2.5%/3.5%/5% respectively. For Aspergillus niger, the increase in the logarithmic reductions as a function of concentration was smaller: 1.5/3.3/3.5 for concentrations of 2.5%/3.5%/5% respectively.

II—Antimicrobial Efficacy of Mixture BEC 721985 a) Bactericidal Activity of BEC 721985 Mixture, 5% by Weight with Respect to the Total Composition

| STRAINS | 1 DAY | 7 DAYS | 14 DAYS | 21 DAYS | 28 DAYS |
|---|---|---|---|---|---|
| Staphylococcus aureus | 1.7 | 2.4 | | 4.4 | 4.7 |
| Escherichia coli | 0.9 | 1.7 | | 3.6 | 3.9 |
| Pseudomonas aeruginosa | 1.5 | 2.9 | | 4.4 | 4.7 |

5% BEC 721985

The BEC 721985 mixture induced a large bactericidal effect from a concentration of 5%, with a logarithmic reduction of more than 3 after 14 days.

b) Fungicidal Activity of BEC 721985 Mixture, 3.5% and 5% by Weight with Respect to the Total Composition

| STRAINS | 1 DAY | 7 DAYS | 14 DAYS | 21 DAYS | 28 DAYS |
|---|---|---|---|---|---|
| Candida albicans | 1.6 | 3.4 | | 3.8 | 4.1 |
| Aspergillus niger | 0.6 | 2.4 | | 3.4 | 3.8 |

3.5% BEC 721985

| STRAINS | 1 DAY | 7 DAYS | 14 DAYS | 21 DAYS | 28 DAYS |
|---|---|---|---|---|---|
| Candida albicans | 0.9 | 1.5 | | 3.6 | 3.8 |
| Aspergillus niger | 0.6 | 2.4 | | 3.5 | 3.6 |

5% BEC 721985

The BEC 721985 mixture induced a large fungicidal effect from 3.5%. Thus for *Candida albicans*, the logarithmic reductions varied from 3.5 to 2.7 for concentrations of 3.5% and 5% respectively. For *Aspergillus niger*, the logarithmic reductions were 2.7 and 3.3 for concentrations of 3.5% and 5% respectively.

III—Antimicrobial Efficacy of Mixture BEC SH a) Bactericidal Activity of BEC SH Mixture 4% and 5% by Weight with Respect to the Total Composition

| STRAINS | 1 DAY | 7 DAYS | 14 DAYS | 21 DAYS | 28 DAYS |
|---|---|---|---|---|---|
| Staphylococcus aureus | 1.6 | 4.5 | | 5.3 | 5.4 |
| Escherichia coli | 1.7 | 4.5 | | 5.3 | 4.3 |
| Pseudomonas aeruginosa | 2.1 | 3.4 | | 5.3 | 4.6 |

4% BEC SH

| STRAINS | 1 DAY | 7 DAYS | 14 DAYS | 21 DAYS | 28 DAYS |
|---|---|---|---|---|---|
| Staphylococcus aureus | 1.8 | 4.4 | | 5.2 | 4.5 |
| Escherichia coli | 2.1 | 4.7 | | 4.4 | 5.2 |
| Pseudomonas aeruginosa | 2.2 | 3.5 | | 4.9 | 4.7 |

5% BEC SH b) Fungicidal Activity of BEC SH Mixture, 4% and 5% by Weight with Respect to the Total Composition

| STRAINS | 1 DAY | 7 DAYS | 14 DAYS | 21 DAYS | 28 DAYS |
|---|---|---|---|---|---|
| Candida albicans | 1.9 | 3.3 | | 5.1 | 7 |
| Aspergillus niger | 1.0 | 3.5 | | 4.8 | 5.2 |

4% BEC SH

| STRAINS | 1 DAY | 7 DAYS | 14 DAYS | 21 DAYS | 28 DAYS |
|---|---|---|---|---|---|
| Candida albicans | 2.3 | 4.5 | | 5.1 | 7 |
| Aspergillus niger | 1.4 | 3.8 | | 5.0 | 7 |

5% BEC SH

IV—Antimicrobial Efficacy of BEC SCS, Mixture 4.5% and 5% by Weight with Respect to the Total Composition a) Bactericidal Activity of BEC SCS

| STRAINS | 1 DAY | 7 DAYS | 14 DAYS | 21 DAYS | 28 DAYS |
|---|---|---|---|---|---|
| Staphylococcus aureus | 0.8 | 3.5 | | 4.6 | 5.2 |
| Escherichia coli | 1.9 | 3.0 | | 4.5 | 4.7 |
| Pseudomonas aeruginosa | 2.1 | 3.4 | | 4.5 | 5.0 |

4.5% BEC SCS

| STRAINS | 1 DAY | 7 DAYS | 14 DAYS | 21 DAYS | 28 DAYS |
|---|---|---|---|---|---|
| Staphylococcus aureus | 1.4 | 3.7 | | 4.8 | 5.3 |
| Escherichia coli | 2.0 | 4.5 | | 4.4 | 5.2 |
| Pseudomonas aeruginosa | 2.2 | 3.4 | | 4.8 | 7 |

5% BEC SCS b) Fungicidal Activity 4.5% and 5% by Weight BEC SCS Mixture with Respect to the Total Composition

| STRAINS | 1 DAY | 7 DAYS | 14 DAYS | 21 DAYS | 28 DAYS |
|---|---|---|---|---|---|
| Candida albicans | 2.3 | 4.6 | | 4.6 | 7 |
| Aspergillus niger | 1.5 | 3.4 | | 4.7 | 4.4 |

4.5% BEC SCS

| STRAINS | 1 DAY | 7 DAYS | 14 DAYS | 21 DAYS | 28 DAYS |
|---|---|---|---|---|---|
| Candida albicans | 1.6 | 5.2 | | 5.1 | 7 |
| Aspergillus niger | 1.7 | 3.5 | | 4.9 | 4.5 |

5% BEC SCS

Incorporation of the α-butylglucoside esters in cosmetic formulae is summarised in the following table:

| α-butyl-glucoside | Formulation | Recommended dose for emulsifying effect | Bactericidal activity | Fungicidal activity |
|---|---|---|---|---|
| BEC 4 | W/O emulsion stable, white, very unctuous | 2.5–5% | From 3.5% | From 2.5% |

-continued

| α-butyl-glucoside | Formulation | Recommended dose for emulsifying effect | Bactericidal activity | Fungicidal activity |
|---|---|---|---|---|
| BEC 721985 | O/W emulsion stable, white, very unctuous | 2.5–5% | From 3.5% | From 3.5% |
| BEC SCS | O/W emulsion stable, white, very unctuous | 2.5–5% | From 3.5% | From 3.5% |
| BEC SH | Hygiene products smooth, foam unctuous, white, satin lustre | 025% to 0.75% | From 2.5% | From 2.5% |

C/Antimicrobial Activity of α-butylglucosides Bactericidal and Fungicidal Properties of α-butylglucoside (α-BG), 0.8% 1%, 3% and 5% by Weight with Respect to the Total Composition

| 0.8% α-butylglucoside | | Logarithmic reduction | | | | |
|---|---|---|---|---|---|---|
| | | 1 d | 7 d | 14 d | 21 d | 28 d |
| Bacteria | Staphylococcus aureus | 1.0 | 2.1 | | 4.0 | 4.0 |
| | Escherichia coli | 1.0 | 2.0 | | 3.1 | 3.2 |
| | Pseudomonas aeruginosa | 1.0 | 1.0 | | 3.2 | 3.3 |
| Yeast | Candida albicans | 0.0 | 2.0 | | 1.3 | 1.3 |
| Fungus | Aspergillus niger | 0.1 | 1.2 | | 3.0 | 3.0 |

| 1% α-butylglucoside | | Logarithmic reduction | | | | |
|---|---|---|---|---|---|---|
| | | 1 d | 7 d | 14 d | 21 d | 28 d |
| Bacteria | Staphylococcus aureus | 1.0 | 2.0 | | 4.1 | 4.2 |
| | Escherichia coli | 0.0 | 2.1 | | 4.1 | 4.2 |
| | Pseudomonas aeruginosa | 1.0 | 2.1 | | 4.3 | 4.3 |
| Yeast | Candida albicans | 0.0 | 1.0 | | 2.0 | 2.0 |
| Fungus | Aspergillus niger | 0.0 | 1.0 | | 2.1 | 3.0 |

| 3% α-butylglucoside | | Logarithmic reduction | | | | |
|---|---|---|---|---|---|---|
| | | 1 d | 7 d | 14 d | 21 d | 28 d |
| Bacteria | Staphylococcus aureus | 1.0 | 2.0 | | 4.0 | 4.1 |
| | Escherichia coli | 0.0 | 2.1 | | 4.1 | 4.1 |
| | Pseudomonas aeruginosa | 1.0 | 2.1 | | 4.1 | 4.1 |
| Yeast | Candida albicans | 0.0 | 2.0 | | 4.2 | 4.2 |
| Fungus | Aspergillus niger | 0.0 | 1.0 | | 3.0 | 2.9 |

| 5% α-butylglucoside | | Logarithmic reduction | | | | |
|---|---|---|---|---|---|---|
| | | 1 d | 7 d | 14 d | 21 d | 28 d |
| Bacteria | Staphylococcus aureus | 1.0 | 2.1 | | 4.1 | 4.1 |
| | Escherichia coli | 1.0 | 2.1 | | 3.3 | 4.1 |
| | Pseudomonas aeruginosa | 1.0 | 2.1 | | 4.2 | 4.2 |
| Yeast | Candida albicans | 0.0 | 2.0 | | 4.2 | 4.2 |
| Fungus | Aspergillus niger | 0.0 | 0.1 | | 1.0 | 1.0 |

The numbers translate as a small reduction in the number of germs for concentrations of less than 0.8%. α-BG corresponds to the bactericidal standards demanded by the "Pharmacopée Française" for concentrations above 1%. A logarithmic reduction of more than 3 was observed after 14 days with no subsequent increase in the number of strains. The bactericidal activity of the α-butylglucoside used in concentrations in the range 1% to 5% thus appears to be effective. It would appear that a bactericidal effect is produced first, followed by a bacteriostatic effect.

Concentrations of 1% to 3% satisfy the fungicidal standards. Surprisingly, a concentration of 5% of α-BG appeared to be less active than at lower concentrations on *Aspergillus niger*. There was thus a "dose effect" concerning the fungicidal power of (α-BG on *Aspergillus niger*.

D/Particular Applications

The bactericidal and fungicidal properties enable α-alkylglucosides, α-alkylglucoside esters and "BEC" mixtures to be used as cosmetic and pharmaceutical active principles in particular for the following uses:

- use in product compositions for hygiene and/or hair treatment, in particular antidandruff shampoos, hair styling products or dyes;
- use in product compositions for hygiene and/or skin treatment, in particular for treating acne, in the form of a cream, milk, gel or perfumed lotion, in bath or shower products, in shaving or makeup products, or in deodorants or antiperspirants.

Beauty, skin care, bath/shower and hair care products can also contain ingredients which are normally used in cosmetics or dermatology, such as perfumes, dyes, other preservatives, sequestrating agents, vegetable, animal or synthetic oils, perfluoropolyethers, hydrating agents, antiwrinkling agents, thinning agents, sun filters, anionic, nonionic, amphoteric or cationic surfactants, polymers, proteins, conditioning agents, foam stabilisers, or propellants.

E/Examples of Compositions

The tables below show compositions comprising active principles as used in the invention. These examples are intended to illustrate the present invention without limiting its scope.

EXAMPLE 1

| PHASE | INGREDIENTS | INT CL NAME | % | SUPPLIER |
|---|---|---|---|---|
| | W/O EMULSION BEC 4/2.5% | | | |
| A | BEC 4 | | 2.5 | SOLABIA ® |
| A | Lanette O | Cetostearylic alcohol | 2 | HENKEL ® |
| A | Cetiol J 600 | Jojoba oil | 3.5 | HENKEL ® |
| A | Ariamol E | PPG 15 stearyl ether | 4 | ICI ® |
| A | Ariamol 812 | Capric/caprylic oil | 5 | ICI ® |
| A | DC 200/350 Cs | Cyclomethicone | 1 | DOW |
| A | Cipol $C_{16}$ | Stearylic alcohol | 2.5 | CORNING ® |
| A | Aerosil 972 | Silica | 0.5 | HENKEL ® |
| A | Titanium dioxide | Titanium dioxide | 10 | DEGUSSA ® |
| A | Propylene glycol | Propylene glycol | 4 | |
| | Fucogel 1000 | biosaccharide Gum-1 | 5 | |
| | Water | | qsp 100 | SOLABIA ® |

EXAMPLE 2

O/W EMULSION BEC 721985/5%

| PHASE | INGREDIENTS | INT CL NAME | % | SUPPLIER |
|---|---|---|---|---|
| A | BEC 721985 | | 5 | SOLABIA ® |
| A | Lanette O | Cetostearylic alcohol | 2 | HENKEL ® |
| A | Cetiol J 600 | Jojoba oil | 3.5 | HENKEL ® |
| A | Ariamol E | PPG 15 stearyl ether | 4 | ICI ® |
| A | Ariamol 812 | Capric/caprylic oil | 5 | ICI ® |
| A | DC 200/350 Cs | Cyclomethicone | 1 | DOW CORNING ® |
| A | Cipol $C_{16}$ | Stearylic alcohol | 2.5 | |
| A | Aerosil 972 | Silica | 0.5 | HENKEL ® |
| B | Propylene glycol | Propylene glycol | 4 | DEGUSSA ® |
| B | Rhodicare T | Canthan Gum | 0.15 | RHONE P ® |
| B | Water | | qsp 100 | |

EXAMPLE 3

0.75% BEC SH FORMULATION

| PHASE | INGREDIENTS | INT CL NAME | % | SUPPLIER |
|---|---|---|---|---|
| G | BEC SH | | 0.75 | SOLABIA ® |
| C | Miracare 2M CASE | Disodium cocoamphodiacetate (and) Sodium lauryl sulphate (and) sodium laureth sulphate (and) propylene glycol | 30 | RHONE P ® |
| B | EDTA | EDTA | 0.10 | |
| D | Dehyton K | Cocoamidopropyl betaine | 5 | HENKEL ® |
| E | Plantarene PS 10 | Sodium laureth sulphate (and) lauryl glucoside | 5 | HENKEL ® |
| F | Comperian LS | Cocoamide DEA (and) Laureth 12 | 1 | HENKEL ® |
| I | Citric acid | Citric acid | 0.4 | |
| H | Germaben II | Propylene glycol (and) Diazolidinyl urea (and) Methylparaben (and) Propylparaben | 0.45 | ISP ® |
| A | Water | | qsp 100 | |

What is claimed is:

1. A method for protecting a composition susceptible to microbial development from microbial development comprising the step of:
adding to a composition susceptible to microbial development at least one antimicrobial agent which is an α-alkylglucoside, an α-alkylglucoside ester or mixtures thereof, wherein the alkyl group of said antimicrobial agent is from 1–6 carbon atoms in length, in an amount which is effective to retard microbial development in said composition.

2. The method according to claim 1, wherein said antimicrobial agent is a fungicide or a bactericide.

3. The method according to claim 1, wherein said antimicrobial agent is provided in an amount of between about 0.5% and about 10% by weight of said composition.

4. The method according to claim 3, wherein said antimicrobial agent is provided in an amount of between about 2.5% and about 5%, by weight of said composition.

5. The method according to claim 2, wherein said antimicrobial agent is a bactericide which includes an α-alkylglucoside ester provided in an amount of at least about 3.5% by weight of the composition.

6. The method according to claim 1, wherein said alkyl group is a butyl group.

7. The method according to claim 1, wherein said antimicrobial agent α-alkylglucoside ester selected from the group consisting of α-butylglucoside mono- or di-caprate, an α-butylglucoside mono- or di-palmitate, and/or α-butylglucoside mono- or di-cocoate.

8. The method according to claim 7, wherein said α-alkylglucoside ester includes at least about 40% by weight, of said antimicrobial agent of an α-butylglucoside ester.

9. The method according to claim 7, wherein said α-alkylglucoside ester includes at least about 80% by weight, of said antimicrobial agent of an α-butylglucoside.

10. The method according to claim 1, wherein said antimicrobial agent includes:

| | |
|---|---|
| a) Polyethylene glycol (30) dipolyhydroxystearate | 15% by weight |
| α-butylglucoside monocaprate | 48% by weight |
| α-butylglucoside dipalmitate | 37% by weight; |
| b) Ester of polyethylene oxide and a fatty alcohol | 40% by weight |
| Ether of polyethylene glycol (21) and stearic alcohol | 15% by weight |
| α-butylglucoside monocaprate | 26% by weight |
| α-butylglucoside monopalmitate | 19% by weight; |
| c) Ester of citric acid and glyceryl sorbitol | 20% by weight |
| α-butylglucoside monocaprate | 46% by weight |
| α-butylglucoside monopalmitate | 34% by weight; or |
| d) α-butylglucoside dicocoate | 48% by weight |
| α-butylglucoside monococoate | 37% by weight |
| α-butylglucoside monopalmitate | 15% by weight, and mixtures thereof. |

11. The method according to claim 2, wherein said antimicrobial agent is a bactericide and includes at least one α-alkylglucoside provided in an amount of between about 0.8% and about 5% by weight of said composition.

12. The method according to claim 2, wherein said antimicrobial agent is a fungicide which includes an α-alkylglucoside provided in an amount of between about 1% and about 3% by weight of said composition.

13. The method according to claim 1, wherein said composition is a cosmetic composition.

14. The method according to claim 13, wherein said cosmetic composition is a hair care product.

15. The method according to claim 14, wherein said hair care product is a dye.

16. The method according to claim 14 wherein said hair care product is a shampoo.

17. The method according to claim 14, wherein said hair care product is an antidandruff shampoo.

18. The method according to claim 1 wherein said composition is a pharmaceutical composition.

19. The method according to claim 18, wherein said pharmaceutical composition is used to treat skin.

20. The method according to claim 19, wherein said pharmaceutical composition is used to treat acne.

21. The method according to claim 13, wherein said cosmetic composition is selected from the group consisting of a bath product, a shower product, a shaving product, a makeup product, a deodorant and an antiperspirant.

* * * * *

UNITED STATES PATENT AND TRADEMARK OFFICE
CERTIFICATE OF CORRECTION

PATENT NO. : 6,475,991 B2
DATED : November 5, 2002
INVENTOR(S) : Emmanuel Boures and Arnaud Messager It is certified that error appears in the above-identified patent and that said Letters Patent is hereby corrected as shown below:

<u>Title page, Item [54] and Column 1, line 3,</u>
"AS ANTI-MICROBIAL AN AGENTS" should be -- AS ANTI-MICROBIAL AGENTS --

<u>Column 4,</u>
Lines 7 through 42, the entire section entitled "BRIEF DESCRIPTION OF THE FIGURES" should be moved to column 1, line 60, before the section entitled "DESCRIPTION OF THE PREFERRED EMBODIMENTS".

<u>Column 10,</u>
Line 16, "cidal power of ($\alpha$-BG on *Aspergillus niger*." should be -- cidal power of $\alpha$-BG on *Aspergillus niger*. --

Signed and Sealed this

Eleventh Day of March, 2003

JAMES E. ROGAN
*Director of the United States Patent and Trademark Office*